(12) United States Patent
Chagoya-Hazas et al.

(10) Patent No.: US 8,507,459 B2
(45) Date of Patent: Aug. 13, 2013

(54) USE OF ADENOSINE ASPARTATE FOR THE PREPARATION OF PHARMACEUTICAL PRODUCTS FOR THE TREATMENT OF LIVER CANCER

(75) Inventors: Victoria-Eugenia Chagoya-Hazas, México (MX); Rolando-Efraín Hernandez Muñoz, México (MX); Saúl Villa-Treviño, México (MX)

(73) Assignee: Universidad Nacional Autonnoma de Mexico, Ciudad Universidad (MX)

( * ) Notice: Subject to any disclaimer, the term of this patent is extended or adjusted under 35 U.S.C. 154(b) by 139 days.

(21) Appl. No.: 12/676,953

(22) PCT Filed: Aug. 21, 2008

(86) PCT No.: PCT/MX2008/000111
§ 371 (c)(1),
(2), (4) Date: Dec. 23, 2010

(87) PCT Pub. No.: WO2009/031876
PCT Pub. Date: Mar. 12, 2009

(65) Prior Publication Data
US 2011/0105425 A1 May 5, 2011

(30) Foreign Application Priority Data

Sep. 6, 2007 (ME) .................. MX/a/2007/010896

(51) Int. Cl.
*A61K 31/70* (2006.01)
*A61K 31/205* (2006.01)
*A01N 37/30* (2006.01)

(52) U.S. Cl.
USPC .......................................... 514/46; 514/566

(58) Field of Classification Search
None
See application file for complete search history.

(56) References Cited

U.S. PATENT DOCUMENTS 5,415,873 A * 5/1995 Trepel et al. .................. 424/422
5,641,500 A * 6/1997 Trepel et al. .................. 424/422

FOREIGN PATENT DOCUMENTS

JP 6228519 A 8/1994
WO 91/16056 A1 10/1991

OTHER PUBLICATIONS

Fishman et al., "The A3 Adenosine Receptor as a New Target for Cancer Chemotherapy and Chemoprotection," Experimental Cell Research, 269(2), 230-236 (Oct. 1, 2001).*
Hernandez-Munox, R., "1131 Effectiveness of aspartate of adenosine as hepatoprotective and anti-fibrotic agent as compared with the parental adenosine" Hepatology, Jan. 2003, vol. 38 (4), pp. 700-701, Baltimore, MD.
Rockelein, G. et al. "Risk factors of hepatocellular carcinoma in Germany: hepatitis B or liver cirrhosis?" Hepatogastroenterology, Aug. 1988, vol. 35, pp151-157.
Bajaj, S. et al., "Adenosine and adenosine analogues are more toxic to chronic lymphocytic leukemia than to normal lymphocytes" Blood, Jul. 1983, vol. 62 (1), pp. 75-80.
Fishman, P. et al., "Adenosine acts as an inhibitor of lymphoma cell growth: a major role for the A3 adenosine receptor" European Journal of Cancer, Feb. 2007, vol. 36, pp. 1452-1458.
Ohana G. et al., "Differential effect of adenosine on tumor and normal cell growth: focus on the A3 adenosine receptor" Journal of Cellular Physiology, 2001, vol. 186, pp. 19-23.

* cited by examiner

*Primary Examiner* — Lawrence E Crane
(74) *Attorney, Agent, or Firm* — Browdy and Neimark, P.L.L.C.

(57) ABSTRACT

The present invention relates to the novel use of an adenosine aspartate product for the formulation of a drug intended to prevent the development of preneoplastic lesions and to reverse some types of cancer, particularly liver cancer, providing chemoprotection, preventing myelotoxic effects.

7 Claims, 5 Drawing Sheets

USE OF ADENOSINE ASPARTATE FOR THE PREPARATION OF PHARMACEUTICAL PRODUCTS FOR THE TREATMENT OF LIVER CANCER

CROSS-REFERENCES TO RELATED APPLICATIONS

This application is the National Stage of International Application No. PCT/MX2008/000111, filed Aug. 21, 2008, and which claims priority of Mexican Patent Application No. MX/a/2007/010896, filed Sep. 6, 2007.

FIELD OF THE INVENTION

The present invention relates to the use of pharmaceutical products to support the therapy against neoplastic diseases, more specifically it relates to a novel use of adenosine salts, as aspartate and prolinate, to prepare drugs to contribute to the therapy against cancer and more specifically to a pharmaceutical formulation to be used alone or in combination with the therapy used against cancer.

BACKGROUND OF THE INVENTION

The adenosine aspartate effect to restore the proliferative capacity of hepatic tissue, stopping the fibrogenesis that occurs in hepatic alterations ending in hepatic cirrhosis, without caring about the aetiological agent, is well known. The adenosine administration in its aspartate salt form, has given beneficial results in controlling cirrhosis of the liver, Mexican patent 207422, reducing the accumulation of collagen remarkably enhancing the histological symptoms of the cryogenic process, which is accompanied by an improvement in the hepatic function tests and the liver energetic parameters. The increase of cell energy availability and collagenolytic activity of the fibrotic liver induced by the adenosine administration, is related to the normalization of the intracellular redox state due to the protection of the mitochondrial function; likewise, it increases the cytochrome p450 making the detoxification processes easier (Chagoya de Sanchez V., Hernández-Muñoz R., Yañez L., Vidrio S., Díaz-Muñoz M. Possible mechanism of adenosine protection in carbon tetrachloride acute hepatoxicity. Role of adenosine by-products and glutathione peroxidase. J., Biochem. Toxicollogy (1995) 10: 41-50). All these changes promote a fast hepatic proliferative response, which is severely depressed in the cirrhotic liver.

It is well known that adenosine aspartate increases the energy metabolism at the expense of the mitochondrial metabolism restoring the normal energy condition reduced by toxic agents that damage the hepatocytes thereby protecting the mitochondrial function and structure. Likewise, its antioxidant effect avoids free radicals propagation and damage caused to proteins and DNA by the hepatotoxic agents. On the other hand, it restores to normal the regenerative response of the cirrhotic liver measured by the activity of thymidine kinase and by the mitotic index. (Hernández-Muñoz R, Díaz-Muñoz M, Suárez-Cuenca J A, Trejo-Solis C, López V, Sánchez-Sevilla L, Yañez L, and Chagoya de Sánchez V. Adenosine reverses a preestablished CCl$_4$—induced micronodular cirrhosis through enhancing collagenolytic activity and stimulating hepatocyte cell proliferation in rats. Hepatology (2001) 34: 677-687.) Likewise, it has been seen that it reduces serum levels of alpha-fetoprotein in cirrhotic patients who present slightly high levels of this hepatic cancer marker; on the other hand, it helps the liver to donate purine backbones to the extrahepatic tissues (Chagoya de Sánchez V, Hernández-Muñoz R, Díaz-Muñoz M, Villalobos R, Glender W, Vidrio S, Suárez J, Yañez L Circadian variations of adenosine level in blood and liver and its possible physiological significance Life Sciences (1983) 33: 1057-1064), this effect generates myeloprotection. Finally, it reorganizes the extracellular matrix by modifying the effect of the adhesion proteins as integrins and adhesins and it induces transformed cell apoptosis, these effects could avoid cancer development and hepatic metastasis. Meanwhile, the effect of a synthetic agonist of the A$_3$ adenosine receptor which inhibits the carcinogenic growth of colon, melanoma, prostate, as well as liver and lung metastasis showing anticarcinogenic and chemoprotective effect has been shown. (Fishman P, Bar-Yehuda S, Barer F, Madi L, Multan A S, Pathak S, The A3 adenosine receptor as a new target for cancer therapy and chemoprotection. Exp Cell Res (2001) 269:230-236.)

From the aforementioned, it is derived that adenosine salts, particularly adenosine aspartate, might be used in a pharmaceutical formulation to prepare drugs for the support therapy of the usual treatment against colon, melanoma, prostate cancer, as well as liver cancer and lung metastasis. In the present invention, given the experience of the research team, it was decided to demonstrate the adenosine aspartate effect mainly in liver cancer, without limiting other kinds of tumors that respond to the activation of the A$_3$ adenosine receptor.

The hepatocellular carcinoma is responsible of 80% to 90% of all the types of liver cancer. Its incidence is greater in men than in women and it attacks mainly people between 50 and 60 years old. This disease is more common in some parts of Africa and Asia than in North America, South America, and Europe. Usually, the cause of liver cancer is cirrhosis or scarring of said organ. Cirrhosis could be caused by viral hepatitis, especially hepatitis B and C, excessive alcohol consumption, certain liver autoimmune diseases, hemochromatosis, and a great number of pathologies.

In order to detect liver cancer, some markers are used, such as γ-glutamyltranspeptidase level measurement called GGT. This test is used to detect liver, bile ducts and kidneys diseases; and also to differentiate liver or bile ducts disorders from bone disease.

GGT takes part in the amino acid transference through the cell membrane and in the glutathione metabolism as well, and this enzyme is in high concentrations in the liver, bile ducts and kidney.

GGT is measured in combination with other tests. Particularly, the alkaline phosphatase is higher in hepatobiliary and bone diseases and GGT is higher in hepatobiliar diseases, but not in bone disease; hence, a patient with a high alkaline phosphatase level and a normal GGT level probably suffers a bone disease but not a hepatobiliar one. Normal values of this marker are in a range of 0 to 5 UI/L, and the higher to normal levels could show congestive heart failure, cholestasis, cirrhosis, ischemia, and hepatic necrosis, hepatic tumor, and hepatitis.

Now then, from knowing the action mechanism and the utility that adenosine aspartate has demonstrated to prevent hepatic cirrhosis, and bearing in mind the existing relationship between this condition and liver cancer development, this invention was developed using adenosine aspartate to formulate a drug to prevent cancer development, mainly hepatic cancer due to its high relationship with cirrhosis. Likewise, when pre-cancerous lesions have been established, adenosine aspartate is used to reverse the process.

(wherein adenosine aspartate was not administered) according to the following: at day 0, diethylnitrosamine (DEN) was administered as carcinogen primer, followed by the administration of 2-acetylaminofluorene (2AAF) as carcinogen promoter at days 7, 8, and 9. At day 10 rats underwent a partial hepatectomy (HP), and at day 25 the animals were sacrificed.

Figure 1:
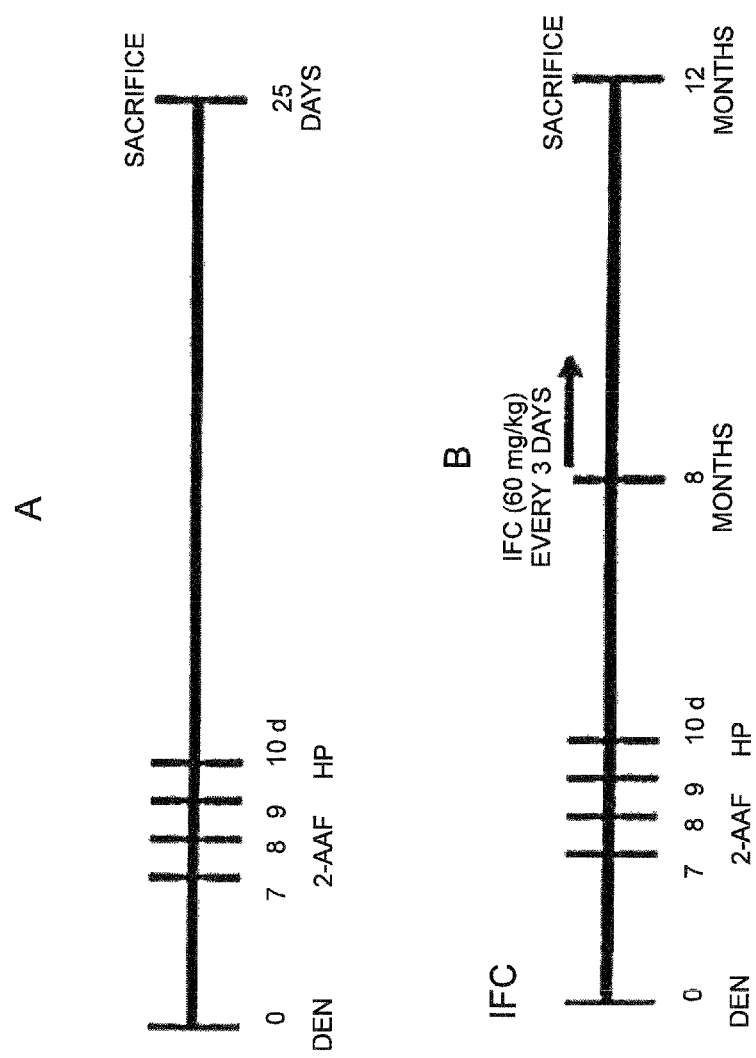
FIG. 1A shows a scheme representing the resistant hepatocyte model of the first experiment described in Example 1

FIG. 1B shows a scheme representing the resistant hepatocyte model of the second experiment of Example 1, wherein adenosine aspartate (IFC) was administered as promoter and primer at day 0, and also from month 8 at a dose of 60 mg/kg every 3 days, until the sacrifice of the animals at month 12.

Figure 2:
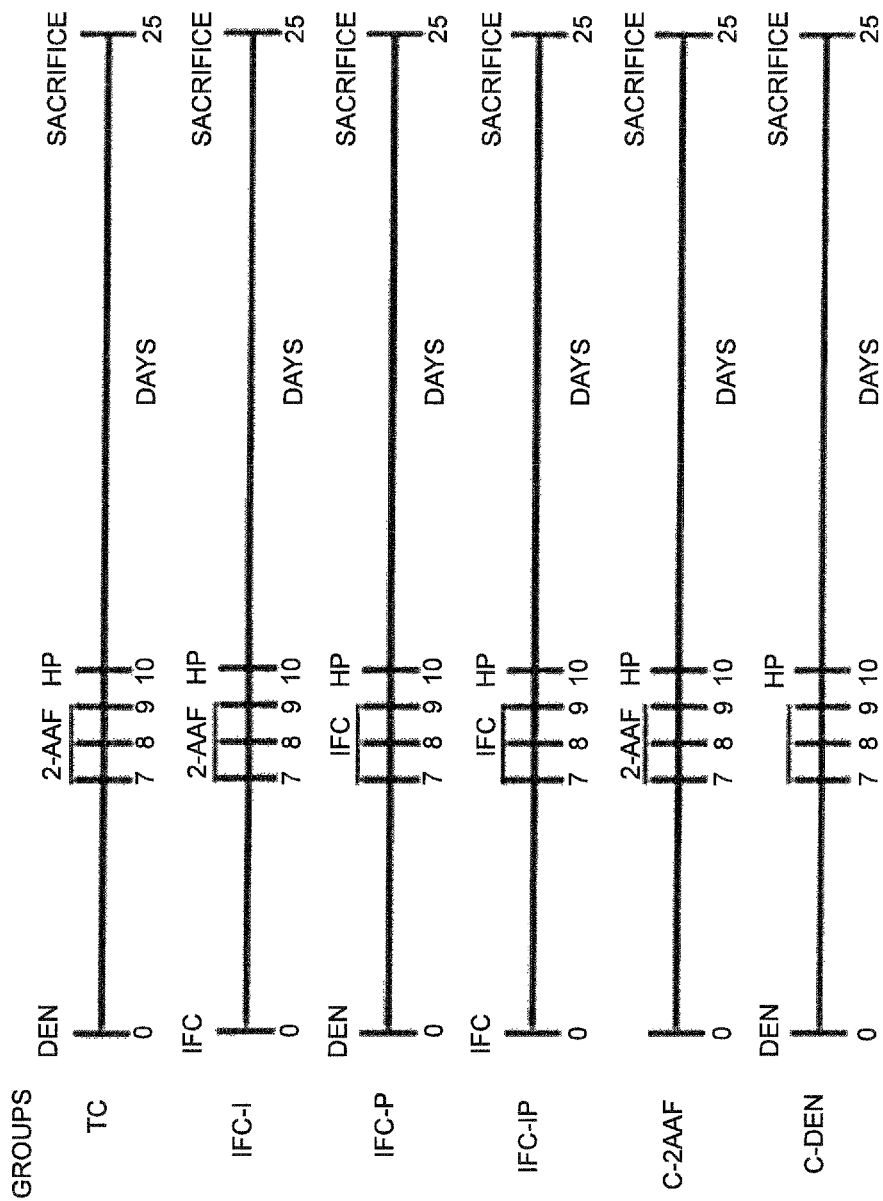

FIG. 2 is a schematic representation showing the treatments to which 6 different testing groups were subjected, according to the Example 2: TC, IFC-I, IFC-P, IFC-IP, C-2AAF and C-DEN. The animals of each group were administered with adenosine aspartate, DEN or 2AAF at days 0, as well as at days 7, 8, 9. At day 10 they were subjected to a HP and they were sacrificed at day 25.

Figure 3:
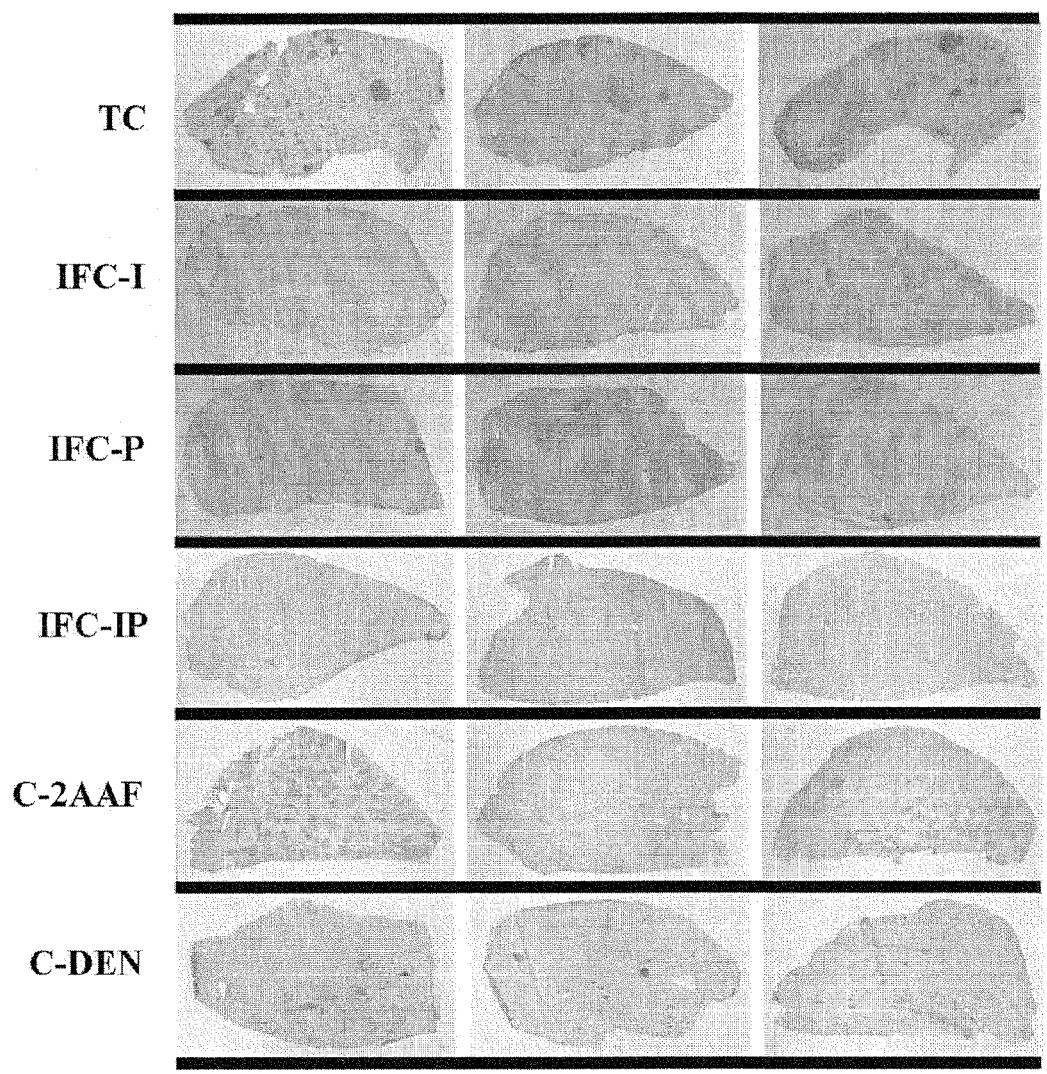

FIG. 3 shows the detection of preneoplastic lesions at each of the 6 experimental groups through histochemical staining of GGT enzyme in sections of rat liver 25 days after the beginning of the experiment. Three sections are showed for each group, wherein preneoplastic lesions are shown as dark dots.

Figure 4:
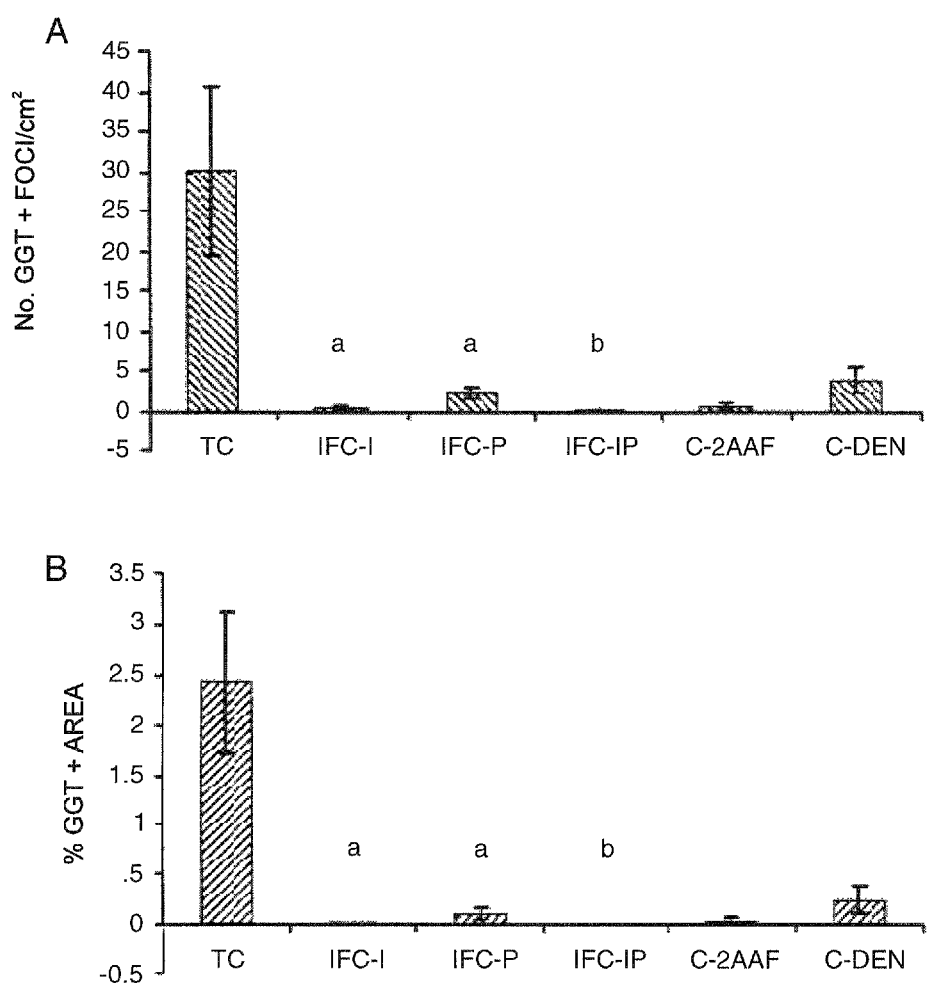

FIG. 4 shows the quantification of preneoplastic foci or lesions, the ordinate axis shows the positive GGT preneoplastic lesion area where it can be seen that in treated groups these foci considerably decrease or disappear. In this (A) means the Number of positive GGT foci/cm$^{2;a}$ significantly different from TC group ($p<0.0001$); $^b$ significantly different from IFC-I groups ($p=0.04$), IFC-P ($p<0.0001$), C-AAF ($p=0.02$), and C-DEN ($p=0.0001$). B means the percentage of the positive GGT area regarding the total tissue; $^a$ significantly different from IC group ($p<0.0001$); $^b$ significantly different from IFC-P groups ($p=0.006$), C-2AAF ($p=0.04$), and C-DEN ($p=0.003$). The results are presented as average values±standard error.

Figure 5:
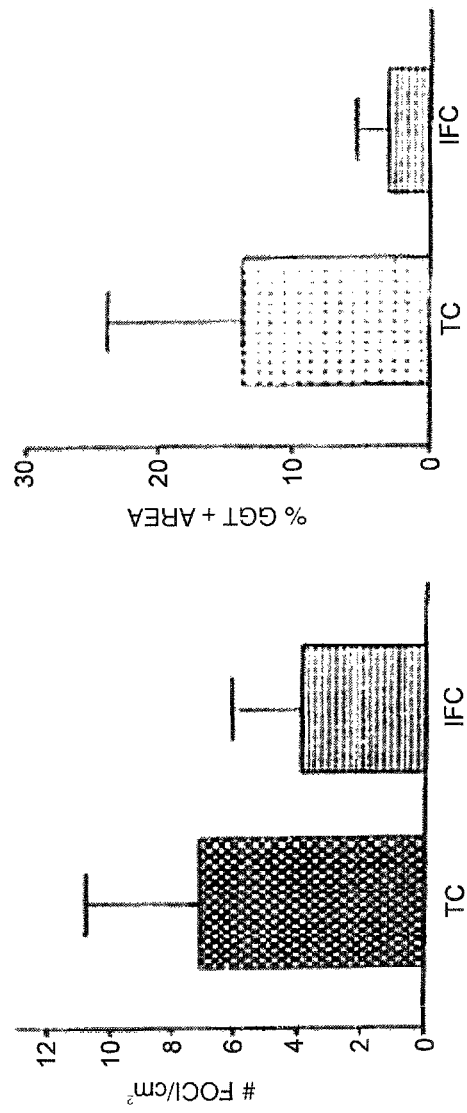

FIG. 5 schematically presents a comparative of TC group with the groups that received adenosine aspartate mentioned as IFC, where the greater amount of preneoplastic lesions as well as the greater percentage of the positive GGT area regarding the total of the treated groups is given in the TC control group.

DETAILED DESCRIPTION OF THE INVENTION

The present invention refers to the use of pharmaceutically acceptable adenosine salts to prepare drugs to support therapy against neoplastic diseases, more specifically as coadjuvant to the therapy against cancer and more specifically to prepare a drug to administer it alone or in combination with the therapy used against cancer in different mammal tissues, preferably in human tissues.

A special feature of the invention is the use of adenosine salts as aspartate, without limiting other adenosine salts, to prepare drugs to prevent and treat neoplastic diseases, or as coadjuvant to the therapy against colon cancer, melanoma, prostate cancer, liver cancer, lung metastasis, without limiting the other types of tumors that respond to the $A_3$ adenosine receptor block.

Drugs prepared with formulations that include adenosine salts of the present invention when administered, at a dose of 750 mg per day, increase the therapeutic index of chemotherapy thus producing myeloprotection.

Physiologically acceptable adenosine salts to prepare drugs which are used to prevent and treat cancer are administered by any suitable administration route, where the pharmaceutical composition is formulated in the suitable pharmaceutical form for the chosen administration route. For the present invention, a preferred embodiment is the administration of the drug orally or by another release route, either regulated or sustained.

The pharmaceutically acceptable excipients, adjuvants, or vehicles which might be used for the formulations that include adenosine salts are the ones known by the skilled in the art and usually used in the drug manufacturing.

EXAMPLES

The following examples are to illustrate the invention but not to limit it. The examples represent the use of adenosine salts to treat rat tissue, which does not limit the invention, since for someone skilled in the art said application might be extended to mammals, among them, humans.

Example 1

The present invention shows the beneficial effect of using adenosine aspartate over neoplastic lesions by carrying out multiple experiments that made possible the evaluation of its protective effect against preneoplastic lesions in rat liver and its reversal effect when the tumor has already developed, using the resistant hepatocyte model. Experiments in groups of animals treated with adenosine aspartate showed that no suggestive alterations of cancer or preneoplastic lesions were present when it was administered after a product used to induce cancer with the resistant hepatocyte model. Animals pretreated with adenosine aspartate did not present specific alterations or preneoplastic lesions compared with control groups, thereby showing that adenosine aspartate has a protective effect against neoplasia development. When the lesion was already installed, it showed the reversal effect thereof.

For the experimental phase in its first stage, male rats of the Fisher 344 strain were used, having 180 to 200 grams body weight, which were bred and kept in an Animal Breeding and Experimentation Unit of the Advanced Research and Studies Center, in a controlled environment with 12-hour cycles of light/darkness at a temperature of 23° C., in hygiene conditions and with free access to food and water. The preneoplastic lesion outgrowth in the liver was induced to the rats by using the resistant hepatocyte model (Semple-Roberts E, Hayes M A, Armstrong D, Becker R A, Racz W J, and Farber E. (1987) Alternative methods of selecting rat hepatocellular nodules resistant to 2-acetylaminofluorence. *Int, J. Cancer.* 40:643-6451) modified by our research group (Carrasc-Legleu C E, Marquez-Rosado L, Fattel-Fazenda S, Arce-Popoca E, Pérez-Carreón JI, VIIIa-Treviño S. (2004) Chemoprotective effect of caffeic acid phenethyl ester on promotion in a medium-term rat hepatocarcinogenesis assay. *Int J. Cancer.* 108:488-92).

As shown in FIG. 1A, a first experiment (TC), without adenosine aspartate, consisted in administering by intraperitoneal route, one single dose of 200 mg/kg of weight of diethylnitrosamine (hereinafter called as DEN) as carcinogen primer. On days 7, 8, and 9 after the beginning, a dose of 20 mg/kg of weight of 2-acetylaminofluorene (hereinafter called as 2AAF) was administered as carcinogen promoter, and on day 10 after the beginning, rats underwent a partial hepatectomy (HP) of 70% of hepatic mass (the administration of these products along with the hepatectomy is taken into consideration as the entire treatment for this experiment). Lastly, the rats were sacrificed at day 25.

The scheme of FIG. 1B shows the administration of adenosine aspartate after a product was used to induce cancer with the resistant hepatocyte model. As can be observed in this figure, this second experiment (IFC) consisted first in administering by intraperitoneal route, one single dose of 200 mg/kg of weight of DEN as carcinogen primer. Additionally, on days 7, 8, and 9 after the beginning, a dose of 20 mg/kg of weight of 2AAF was administered as carcinogen promoter, and on day 10 after the beginning, rats underwent an HP. In addition, adenosine aspartate was administered at day 0 and from the month 8 at a dose of 60 mg/kg, every 3 days. The rats were sacrificed at month 12.

As previously mentioned, animals treated with adenosine aspartate showed that when preneoplastic lesions were already installed, it showed the reversal effect thereof.

Example 2

In order to show the beneficial effect of adenosine aspartate in preneoplastic lesions, 6 different experimental groups were designed, as shown in FIG. 2.

The first group (TC), having 8 rats, was administered with the entire treatment; this group was used as positive control of the preneoplastic lesion outgrowth. The second group (IFC-1), having 8 animals, was administered with a pharmacologically effective dose of adenosine aspartate, which for this case, was 50 mg/kg of body weight dissolved in a physiological saline solution, pH 7.4 with 0.5% carboxymethyl-cellulose, replacing DEN carcinogen primer. The third group (IFC-P), having 8 animals, was administered with a pharmacologically effective dose of adenosine aspartate, which for this case, was 50 mg/kg of body weight dissolved in a physiological saline solution, pH 7.4 with 0.5% carboxymethyl-cellulose, replacing 2-AAF carcinogen promoter. In the fourth group (IFC-IP), with 7 animals, both the DEN carcinogen primer and the 2AAF carcinogen promoter were substituted by adenosine aspartate in pharmacologically effective doses, which in this case, was 50 mg/kg of body weight dissolved in a physiological saline solution, pH 7.4 with 0.5% carboxymethyl-cellulose. The fifth group (C-2AAF), having 6 animals, was administered with 2AAF only, being used as control of the administration of adenosine aspartate at the beginning of the second group (IFC-I. Finally, the sixth group(C-DEN), having 7 animals, which received DEN product only, was used as control of the administration of adenosine aspartate in the promotion of group 3 (IFC-P).

When ending the cycle, all groups underwent a partial hepatectomy. Lastly, all rats were sacrificed 25 days after the beginning of the experiment and their liver was removed to evaluate the appearance of preneoplastic and neoplastic lesions through the histochemical detection of the γ-glutamil-transpeptidase marker (GGT), detected in a 15 µm thick section of frozen liver, histochemically stained to reveal the activity of the GGT enzyme according to Rutengurg method (Rutenburg A M, Kim H, Fischbein J W, Hanker J S, Wasserkrug H L and Seligman A M. (1969) Histochemical and ultrastructural demonstration of γ-glutamiltranspeptidase activity. *J. Histochem. Cytochem.* 17(8):517-526.) Briefly, sections were set in absolute ethanol for 10 min at −20° C.; subsequently, they were treated with a solution that contains 125 µg/ml of γ-glutamil-4-methoxi-2-naphthylamide (GMNA), 0.5 mg/ml of glycyl-glycine and 0.5 mg/ml of Fast Blue in 100 mM of Tris base and they were incubated for 30 minutes at room temperature; finally, they were washed with saline solution, the precipitated were set with 100 mM cupric sulfate solution. All reagents acquired from Sigma Chemical Co. in St Louis, Mo., USA. The enzyme activity was expressed in areas stained with dark red color. GGT is a marker widely used to detect preneoplastic lesions in rat liver, it is absent in hepatocytes of adult rats, while in altered hepatocytes the expression noticeably appears (Hanigan M H. (1988) γ-Glutamyl transpeptidase, a glutathionase: its expression and function in carcinogenesis. *Chemico-Biological interactions.* 111-112:333-342.)

Results can be observed in FIG. 3, where TC group presents the highest amount of preneoplastic lesions as well as the highest percentage of positive GGT area regarding the total of the groups treated with the adenosine aspartate compound, as it is specifically shown in FIG. 5.

When adenosine aspartate was administered as primer in group two, IFC-I or as IFC-P promoter in group three according to the treatment scheme mentioned in FIG. 2, it had no effect over the preneoplastic lesion outgrowth compared with its respective control groups, fifth C-2AAF and sixth C-DEN groups, this situation can be schematically observed in FIG. 4. Finally, when adenosine aspartate was administered as primer and as promoter in fourth IFC-IP group, no preneoplastic lesions were developed. It is important to say that when adenosine aspartate was administered as carcinogen primer in group 2 IFC-I, some livers presented positive GGT arborescences, which were also observed in fifth group used as C-2AAF control; on the contrary, when adenosine aspartate was administered as carcinogen promoter in group three IFC-P, positive GGT arborescences were not observed but small preneoplastic lesions were observed just like in sixth group used as C-DEN control.

The preneoplastic lesions quantification revealed that positive TC control group that received the entire treatment, reached a 30.06% foci/cm$^2$ average and a positive total GGT area percentage of 2.41%. If we take these numbers into account as 100%, in group two where adenosine aspartate was administered as IFC-I primer, the average of foci/cm$^2$ was 1.3% and the positive GGT area of 0.4% regarding the control group with the entire treatment. When adenosine aspartate was administered as promoter in group three IFC-P, the average of foci/cm$^2$ was 7.1% and the positive GGT area of 4.6% regarding the control group with the entire treatment. The alterations in the prior two groups were lower in number as well as in area, compared with fifth and sixth control groups C-2AAF and C-DEN respectively. In the group where adenosine aspartate was administered as primer and as group four IFC-IP promoter, the number of foci/cm$^2$ was 0.2% and the GGT positive area was 0.08% regarding the control group with the entire treatment.

With the aforementioned, it is shown that adenosine aspartate has a protective effect over the preneoplastic lesion development and because of this it protects against cancer development and it also presented a reversal effect of the tumor when cancer was already developed.

In humans, the adenosine aspartate is administered preferably in doses of 750 mg per day in simple dosage of 250 mg distributed in three oral doses, although this dose could be adjusted trying to get the pharmacological effect mentioned herein with lower amounts or in sustained release formulations without appearance of non desirable cardiovascular effects that could be with the administration of this product.

The invention claimed is:

1. A method of inhibiting the outgrowth of preneoplastic lesions of the liver, which comprises administering to a patient in need thereof a therapeutically effective amount of adenosine aspartate, wherein the patient is not suffering from cirrhosis of the liver.

2. The method according to claim 1, wherein the adenosine aspartate is administered at a dose of 750 mg per day.

3. The method according to claim 1, wherein the adenosine aspartate is administered with pharmaceutically acceptable excipients, adjuvants or vehicles, by oral or parenteral route.

4. The method according to claim 1, wherein the patient is human.

5. The method of claim 1 wherein said inhibiting of outgrowth results in inhibition of the development of liver cancer.

6. The method of claim 5 wherein the liver cancer is a hepatocellular carcinoma.

7. A method of inhibiting the outgrowth of preneoplastic lesions of the liver, which comprises administering to a patient in need thereof a therapeutically effective amount of adenosine aspartate, wherein the adenosine aspartate is administered at a dose of 750 mg per day.

* * * * *